United States Patent [19]
Saadatmanesh et al.

[11] Patent Number: 5,396,571
[45] Date of Patent: Mar. 7, 1995

[54] COUPLING DEVICE AND METHOD FOR IMPROVED TRANSFER EFFICIENCY OF LIGHT ENERGY FROM A LASER SOURCE INTO OPTICAL FIBERS

[75] Inventors: Vahid Saadatmanesh, Irvine; Marvin P. Loeb, Huntington Beach, both of Calif.

[73] Assignee: Trimedyne, Inc., Irvine, Calif.

[21] Appl. No.: 65,638

[22] Filed: May 21, 1993

[51] Int. Cl.⁶ .............................................. G02B 6/32
[52] U.S. Cl. ........................................ 385/33; 385/89; 385/93
[58] Field of Search ........................ 385/33, 34, 35, 36, 385/37, 22, 89, 93

[56] References Cited

U.S. PATENT DOCUMENTS

| | | |
|---|---|---|
| 4,795,227 | 1/1989 | Chande ................................. 385/33 |
| 4,961,622 | 10/1990 | Gorman et al. ...................... 385/33 |

FOREIGN PATENT DOCUMENTS

| | | | |
|---|---|---|---|
| 2415046 | 10/1975 | Germany ............................. 385/33 |
| 63-163417 | 7/1988 | Japan .................................. 385/33 |
| 63-291012 | 11/1988 | Japan .................................. 385/33 |
| 1-24209 | 1/1989 | Japan .................................. 385/33 |
| 4-116507 | 4/1992 | Japan .................................. 385/33 |

*Primary Examiner*—Rodney B. Bovernick
*Assistant Examiner*—John Ngo
*Attorney, Agent, or Firm*—Olson & Hierl, Ltd.

[57] ABSTRACT

Optical coupling devices for an improved coupling efficiency of light energy, without damage to the optical components, are disclosed. An optical system divides an input beam of light energy into two or more output beams of lesser energy, each of which is focused toward a focal point in space. Individual optical fibers are positioned with their proximal end faces at the focal points of each of the lesser output beams. Means for dividing the light energy and aligning the components are disclosed.

17 Claims, 8 Drawing Sheets

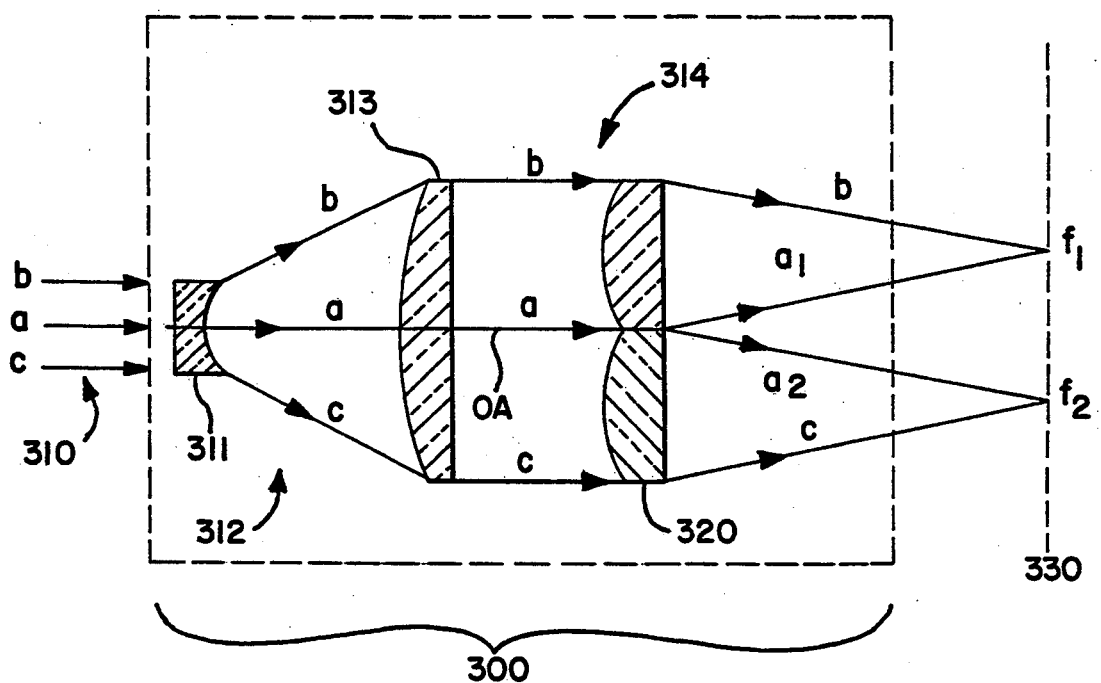
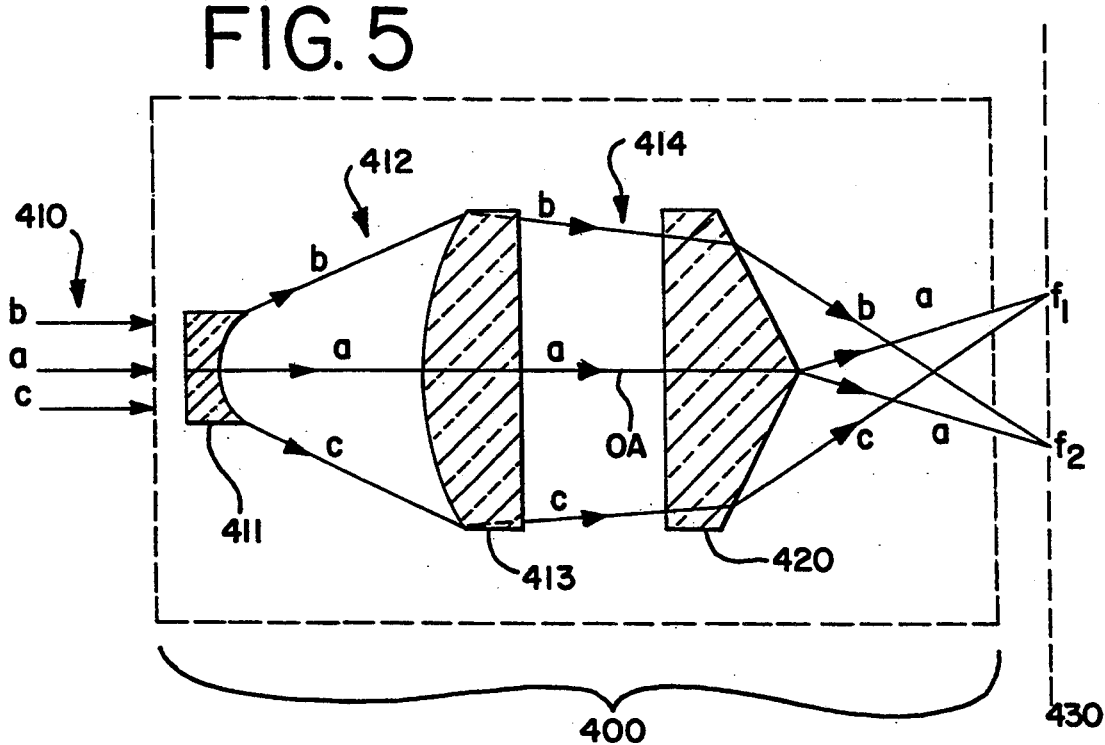

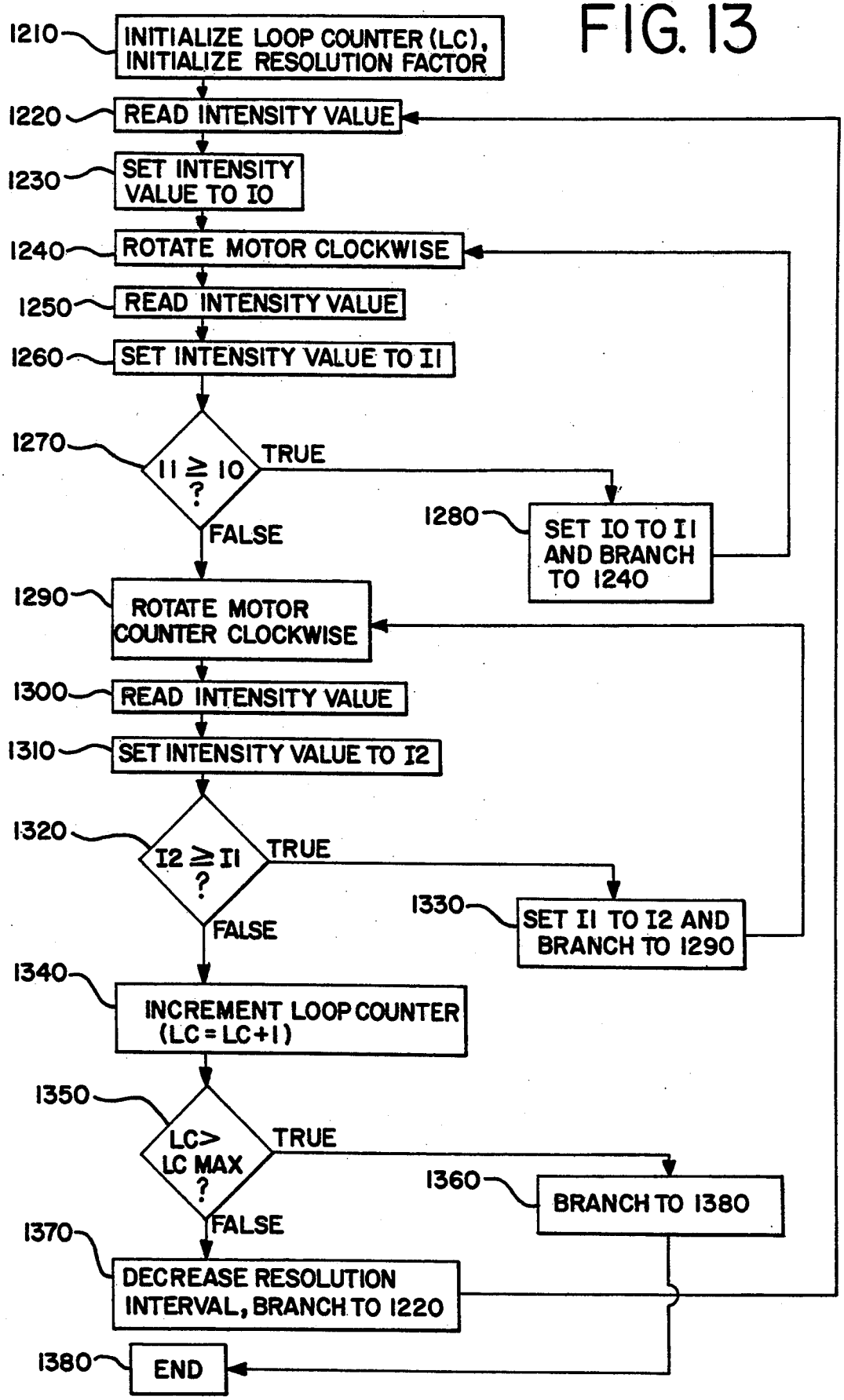

COUPLING DEVICE AND METHOD FOR IMPROVED TRANSFER EFFICIENCY OF LIGHT ENERGY FROM A LASER SOURCE INTO OPTICAL FIBERS

BACKGROUND OF THE INVENTION

1. Field of the Invention

The present invention relates to the field of optical couplers. In particular, the present invention relates to optical fiber coupling devices that convert a single input beam of light energy from a laser into multiple output beams of partial light energy, each of which is focused into a separate optical fiber, with improved transfer efficiency and without damage to the individual optical fibers.

2. Description of the Prior Art

Many applications for laser energy in medicine are known in the prior art. Lasers produce an intense, coherent, directional beam of light energy. Medical applications of lasers include coagulating bleeding ulcers, removing plaque (a fatty deposit) in a blood vessel, excising or vaporizing a tumor, and ablating the hard dentin or enamel of a tooth, to name a few. In order to transmit light energy needed for these surgical applications, optical fibers made of transparent materials, such as glass, fused silica or the like, are utilized to channel and direct the energy. Either a single discrete fiber or a bundle of fibers may be used to transmit the light energy.

A relatively large diameter optical fiber, such as one with a core diameter of 1,000 microns, can transmit a relatively great amount of light energy without damage to the integrity of the optical fiber. However, where flexibility is needed, for example, to enable the optical fiber to pass through a tortuous blood vessel or to reach a relatively inaccessible site in a body behind other structures, a single, relatively large diameter optical fiber may not be sufficiently flexible. While a relatively smaller diameter optical fiber, such as one with core diameter of 50 or 100 microns, may provide more flexibility, a small diameter optical fiber is often unable to carry a sufficiently large amount of light energy without significant damage to the optical fiber.

To transmit large amounts of light energy, while retaining needed flexibility, it is frequently necessary to use a plurality of smaller diameter optical fibers in a bundle, thereby dividing the light energy into several parts so that the energy carried by each individual optical fiber is not excessive. The use of multiple optical fibers, each carrying a portion of the light energy needed to accomplish the desired result, is particularly advantageous, for example, in the transmission of extremely high intensity pulsed light energy from a xenon chloride (excimer) laser at a wavelength of 0.308 microns through quartz or fused silica optical fibers with a high hydroxyl content, or from a holmium:YAG laser at a wavelength of 2.1 microns, through quartz or fused silica optical fibers with a low hydroxyl content. It would be desirable to transmit light energy from an erbium:YAG laser at a wavelength of 2.94 microns. However, light energy of this wavelength cannot be efficiently transmitted through conventional quartz or fused silica fibers. Zirconium fluoride fibers, the fibers of choice for that purpose, can transmit only a small amount of said light energy without fracturing or melting and-releasing toxic gas.

In delivering light energy from a laser to a bundle of fibers, there are significant losses of light energy. This is part of the problem that the present invention addresses. Primarily, the energy losses occur because the emitted laser beam is focused on a cross section of fibers in the bundle, and a portion of the light energy is lost in the spaces between the fibers as well as in the cladding which surrounds each fiber. Furthermore, where the laser emission is in a gaussian pattern, the fibers in the center of the bundle receive a larger amount of light energy than those in the periphery of the bundle.

Since many applications require the delivery 10 of more light energy than one optical fiber of relatively small diameter can effectively and safely transmit, it would be useful to have a device which could divide the light energy from a single laser source into a plurality of relatively equal individual beams, with each beam independently directed toward an individual focal point, so that the proximal end faces of a corresponding plurality of individual optical fibers could each be positioned at one of the focal points. Since each optical fiber would be individually positioned to receive a proportionate amount of the light energy from the partitioned beam, the device would avoid the substantial losses of light energy associated with the coupling inefficiencies in the past. In addition, since the method of light beam partitioning would divide the light energy into relatively equal, separate parts, below the damage threshold of the receiving optical fiber, each of the individual fibers in the bundle could receive and transmit an equal amount of laser light energy without damage thereto.

However, the division of laser light energy into the individual fibers in the bundle does not necessarily need to be equally distributed; nor does the predominant spectral line that is delivered to each individual fiber need to be the same wavelength. Also, by focusing the light energy delivered to each individual optical fiber, the light energy could be delivered to each individual optical fiber with a spot size area and convergence angle which is most suitable for entry into that optical fiber.

Therefore, there is a need for a light energy coupling device and method to divide light energy from a single transmission path into a plurality of transmission paths; where the plurality of individual transmission paths are directed toward and focused into a corresponding plurality of individual optical fibers; and, where the light energy directed into each optical fiber does not exceed its damage threshold. The present invention satisfies the foregoing needs.

The following patents describe light energy coupling devices and methods.

U.S. Pat. No. 4,933,949, to Johnson (hereafter the "Johnson Patent") for "Arrangement for Multiplexing and Intensity Splitting Light Beams for Interface into Fiber Optic Cables".

U.S. Pat. No. 4,961,622, to Gorman et al. (hereafter the "Gorman Patent") for "Optical Coupler and Refractive Lamp".

U.S. Pat. No. 4,868,361, to Chande et al. (hereafter the "Chande Patent") for "Coupling Device for High Power Laser Beam Transmitting Optical Fibers".

U.S. Pat. No. 4,917,084, to Sinofsky (hereafter the "First Sinofsky Patent") for "Infrared Laser Catheter System".

U.S. Pat. No. 4,950,266, to Sinofsky (hereafter the "Second Sinofsky Patent") for "Infrared Laser Catheter System".

U.S. Pat. No. 4,925,265, to Rink et al. (hereafter the "Rink Patent") for "Apparatus for Directing a Laser Beam into Optical Fibers".

The Johnson patent discloses an optical mixing bar of sufficient length to permit mixing of light therein. The mixing bar has a plurality of facets on the beam input end. There are means for directing separate laser beams into each of the facets of the mixing bar. The light energy mixes within the mixing bar and the output of the mixing bar is a single beam of laser light energy approximately equal to the sum of the energies of the input beams. In the present invention, there is a single light energy beam at the input, and that beam is permitted to pass through an optical system that separates the light into a plurality of separate open or free beam paths that converge at a plurality of associated focal regions. In contrast, the Johnson patent teaches to combine a plurality of mixed input beams into plural output beams, a different purpose than that contemplated by the present invention. In addition, the present invention permits fine mechanical positioning of the multiple output beams to enhance their alignment into the individual optical fibers.

The Gorman Patent discloses an optical coupler and refractive lamp. The Gorman Patent describes an optical system that produces an input ring of laser light energy. A plurality of optical fibers are arranged concentrically in a ring opposite the ring of laser light energy. The present invention is an improvement over the Gorman Patent, because the present invention focuses a portion of the input energy precisely into each of a plurality of individual optical fibers, thereby increasing the transmission efficiency.

The Chande patent discloses an optical system for coupling a high power laser beam from one optical fiber into another optical fiber. There is a mounting means, so that both the input optical fiber and the output optical fiber can be retained in alignment. The Chande patent is different from the present invention, in that the present invention transmits the input light energy from a single source into a plurality of output optical fibers. In contrast, the light energy coupling in the Chande patent is limited to transmitting light energy from a single input fiber into another single output fiber.

The Sinofsky patents disclose an infrared laser catheter system which is utilized for the percutaneous removal of atherosclerotic plaque. A single beam of light energy is directed toward the proximal ends of several optical fibers. In the four-fiber coupling system of the Second Sinefsky patent, a portion of the laser light is transmitted into four mirrors, each of which reflects the laser light into one of four lenses, that each focus the light energy into one of four optical fibers that are retained in four fiber optic connectors. In contrast, in the present invention, the beam is partitioned and individually directed into a plurality of optical fibers. The present invention utilizes fewer optics than the Sinofsky invention. Also, it is not necessary for the single input beam of the present invention to be divided by mirrors or beam splitters, as taught by the Sinofsky patents. In addition, the present invention provides increased coupling efficiency.

The Rink patent discloses an apparatus for directing a laser beam into optical fibers. The apparatus utilizes a movable lens which steers the beam serially into individual optical fibers. In contrast, the present invention utilizes optics in a fixed position, the output of which is focused into individual optical fibers. The present invention differs from the Rink patent, in that a single path of light energy in the present invention is simultaneously divided and focused into a plurality of open or free beam paths without moving parts.

None of the aforementioned prior art has implemented an optical coupling device and method where the light energy is transferred from a single source and along a single transmission path into a plurality of open or free beam transmission paths by a partitioning optical system, where the plurality of transmission paths are directed toward and focused into a corresponding plurality of optical fibers, and where the energy directed into each optical fiber does not exceed its damage threshold; all in a manner that improves the transfer efficiency of the optical coupling without moving parts.

SUMMARY OF THE INVENTION

The present invention provides an effective optical fiber coupling device and method for improved coupling of a relatively large amount of light energy from a laser source.

The input light energy is usually derived from a narrow, coherent, high energy beam of light from a laser source. It is also possible for the input light energy to carry more than one spectral line component. The present invention can be configured to optically filter specific spectral line components from the incident light energy. The optical system can also include a means to expand the cross sectional area of the input light energy beam, reducing the energy density thereof, to prevent damage therefrom to the proximal surface of the optical system.

To that end, the present invention entails an optical system that divides an input beam of light energy from a laser source into two or more portions, each of which portions is focused and can be delivered, with minimal loss of energy, into a separate optical fiber. The dividing or partitioning optical component can be positioned in the input beam of light energy at a region where the energy density is below the damage threshold of the proximal surface of the dividing or partitioning optical component. Furthermore, since each of the separate output beams carries only a portion of the light energy, damage to the proximal surface of each energy receiving optical fiber is minimized or eliminated. The amount of light energy transmitted through each optical fiber is maintained at a level which is within the transmission capability of the individual optical fiber.

The contemplated coupling device includes an optical system means and a plurality of fiber optics. A focusing means for each optical fiber can also be utilized, as well as an input beam diverging or converging means.

The optical system partitions the light energy emitted from a laser source into a plurality of lesser laser beams about an optical axis. The plurality of fiber optics constitute a substantially coplanar array with the end faces of the optical fibers arranged about the aforesaid optical axis and at a fixed distance from the optical system means. Each of the end faces defines an incident beam cone of acceptance for one of the aforementioned lesser beams. The number of end faces in the array preferably is equal to the number of the aforesaid partitioned light energy beams. While the number of end faces can vary, at least one such end face is always present to receive a lesser laser beam.

A separate focusing means can be employed to direct each of the divided beams into the end face of one of the optical fibers within the cone of acceptance for that end face. Additionally the diameter of the input beam of light energy can be expanded or contracted by a beam diverging or converging means to reduce the energy density and avoid damage to the proximal surface of the optical system means.

The light energy emitted from the distal ends of the plurality of optical fibers, which may be bundled together or spaced apart in an annular array or other desired configuration, can be directed toward a target. Alternatively, a collector means may be used to recombine the plurality of beams of light energy into one beam for direction toward a target.

Additional advantages and novel features are set forth in the description which follows. Still other advantages and features will become apparent upon examination of the following specification or may be learned by practice of the invention. The advantages and features, including variations of the present invention not specifically disclosed, may be realized by those skilled in the art and attained by means of the instrumentalities and combinations particularly pointed out in the appended claims.

BRIEF DESCRIPTION OF THE DRAWINGS

FIG. 4 is a ray trace diagram of an optical system that utilizes a two-segmented lens to divide the beam of light energy toward a pair of focal points;

FIG. 5 is a ray trace diagram of an optical system which utilizes a two-faceted lens to divide the beam of light energy toward a pair of focal points;

FIG. 13 is a computer program flowchart, used in conjunction with the feedback control system of FIG. 12, to find the maximum signal intensity for correct alignment of each of the optical fiber end faces.

DETAILED DESCRIPTION OF THE PREFERRED EMBODIMENTS

The present invention provides an optical fiber coupling device and method for improved transfer efficiency of light energy from a laser source concurrently into a plurality of optical fibers. The efficiency, laser energy, power and spectral characteristics, with respect to the advantages of the present invention, are identified. The distribution of a laser beam of light energy into a plurality of optical fibers is accomplished by means of specialized optical components, such as a multi-faceted lens, a multi-segmented lens or a multi-segmented mirror. The optical system utilized in practicing the invention is described in detail through ray trace diagrams and a general outline of the geometry of the optics. The arrangement of the components, including the means to align and retain each of the elements in cooperation, are clearly outlined in the ensuing text and illustrations.

Figure 1:
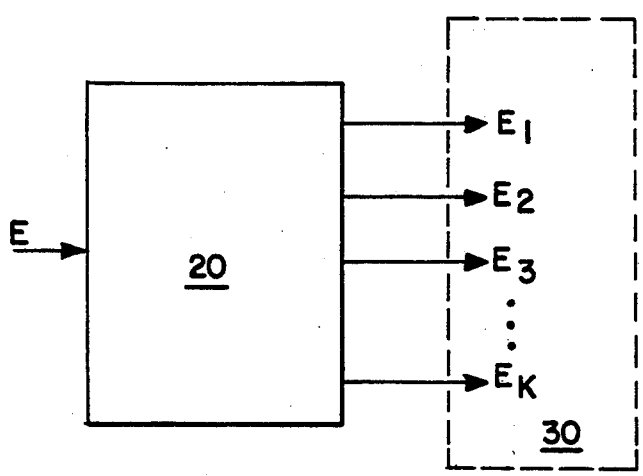
FIG. 1 is a block diagram illustrating, schematically, energy transfer through an optical system from a single input source to a plurality of output energy beams.

Referring to FIG. 1, representative incident light energy E, is transmitted through the optical system 20 and exits as a plurality of partial light energies E1, E2, E3 . . . Ek, denoted by legend 30. The additive sum of the partial light energies E1, E2, E3 . . . Ek will always be less than the incident light energy E, because all optical systems are characterized by losses, primarily due to absorption, reflection and scattering of the light energy, as well as losses due to misalignment of the optical components.

Transfer efficiency is defined as the ratio of the sum of the partial light energies E1, E2, E3 . . . Ek, to the incident light beam energy E. In a realized system, the incident light energy E is introduced at an input port and the partial light energies E1, E2, E3 . . . Ek exit at a plurality of output ports. Incident light energy E and each of the partial energies E1, E2, E3 . . . Ek, at the output of the optical system 20, can be measured with a detector, such as an integrating sphere, a joule meter or a power meter, as known in the art.

Energy is defined as the capacity for doing work. Energy content is commonly used to characterize the output from pulsed lasers, and is generally expressed in joules. Power, as applied to lasers, is also defined as the time rate at which energy is emitted, transferred, or received: usually expressed in watts (or in joules per second).

Standard terms, as applied to lasers and optical fibers, and as used herein, are defined in the *"IEEE Standard Dictionary of Electrical and Electronics Terms"*, ANSI/IEEE Std 100–1984, published by The Institute of Electrical and Electronics Engineers, Inc., N.Y., N.Y., and distributed in cooperation with Wiley-Interscience, a division of John Wiley & Sons, Inc.

Efficiency, in general, is the ratio of the useful output energy to the input energy. Quantum efficiency, in an optical source or detector, is the ratio of output quanta to input quanta. In a simplified model (where the quanta are photons), quantum efficiency is defined as the ratio of the number of photons at the output to the number of photons at the input. However, it is recognized that photons are generally measured through observation of semiconductor photoconductivity, by establishing the rate at which free carriers are generated, determining the mobility of the carriers, and by measuring the length of time they persist in conductive states due to the exposure to radiant energy. The energy of each photon is given by the product of Plank's constant and the optical frequency. The concept of quantum efficiency, including the relationship between the photons and electrical conductivity, is important for monitoring the light energy and for determination of actual energy losses in the system.

The optical system 20, can have light energy transfer characteristics which transmit, converge or diverge, and refract the light energy according to the geometric shape, the index of refraction and absorption characteristics of the optical substrate and the optical coating. Many high precision optics have thin film anti-reflective coatings designed to selectively transmit any number of specific frequencies or frequency bands of light energy with increased efficiency. Certain exotic multi-layer anti-reflective coatings can transmit more than ninety nine percent of the incident light through the application of alternating combinations of thin film dielectric materials of high index and low index of refraction. Multilayer coatings can also narrow the transmission of a frequency band.

In the present invention, the optical system 20 is designed to improve the transmission efficiency of light energy from a laser into a plurality of flexible, small core diameter optical fibers for carrying the light energy to a target without damage to the flexible fiber optic means.

Lasers used in surgical applications are generally monochromatic, consisting of a single wavelength or a narrow band of wavelengths, such as: the CO2 laser at a wavelength of 10.6 microns, the erbium:YAG laser at a wavelength of 2.94 microns, the holmium:YAG laser at a wavelength of 2.09 microns, the Nd:Yag laser at a wavelength of 1.064 microns, the argon laser at 488 to 514 microns, the xenon chloride (excimer) laser at a wavelength of 0.308 microns, or the argon fluoride (excimer) laser at a wavelength of 0.193 microns, among others. Laser energy is generally considered to be coherent for finite distances; such regions of coherence exist where the phase relationship between points on the electromagnetic wave is fixed.

In the present invention, light energy E is divided by the optical system 20 into partial light energies E1, E2, E3 ... Ek and are focused into a corresponding plurality of fiber optics. Each fiber optic has a particular cone of acceptance and absorption characteristic. Laser induced damage to the fiber optic could result if the proximal end face of the fiber optic is exposed to an excessive level of irradiance (power density, expressed in joules per square centimeter of surface area). The fiber optic may also fault at the site of impurities and defects therein, as well as at the proximal end face thereof.

Since excimer, erbium:YAG and certain other lasers create beams of light energy whose density may exceed the damage threshold of an-available fiber optic, the present invention is particularly useful with such lasers. Also, since such lasers create beams of light energy whose density may exceed the damage threshold of the incident surface of a lens, the dividing or partitioning optical means may be positioned at a point in the input beam of light energy where the energy density is below its surface damage threshold, and the dividing or partitioning optic means can be sized to capture substantially all of the light energy in the input beam, increasing the coupling efficiency.

Figure 2:
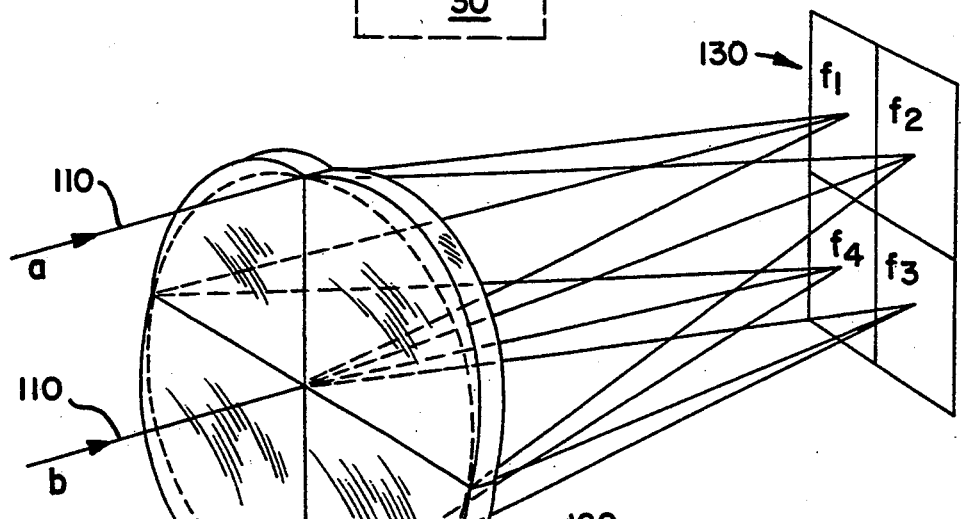
FIG. 2 is a perspective, schematic view of a collimated beam of light energy divided by a multi-segmented lens into four focal points in a single focal plane.

Referring to FIG. 2, a perspective view of a multi-segmented lens 120 is shown. The multi-segmented lens 120 is utilized to divide a light beam 110 into a plurality of partial light energies, as illustrated in FIG. 1. The light beam 110, with generally parallel light rays a, b and c, is transmitted through the multi-segmented lens 120 which divides the light beam 110 into four separate beams that converge along an open or free beam path at a focal point (f1, f2, f3 and f4, respectively) in space. Preferably, the four focal points (f1, f2, f3, and f4) lie in the same focal plane 130, i.e., the focal points are coplanar. A lens with a larger or smaller number of segments performs in the same manner.

Figure 3:
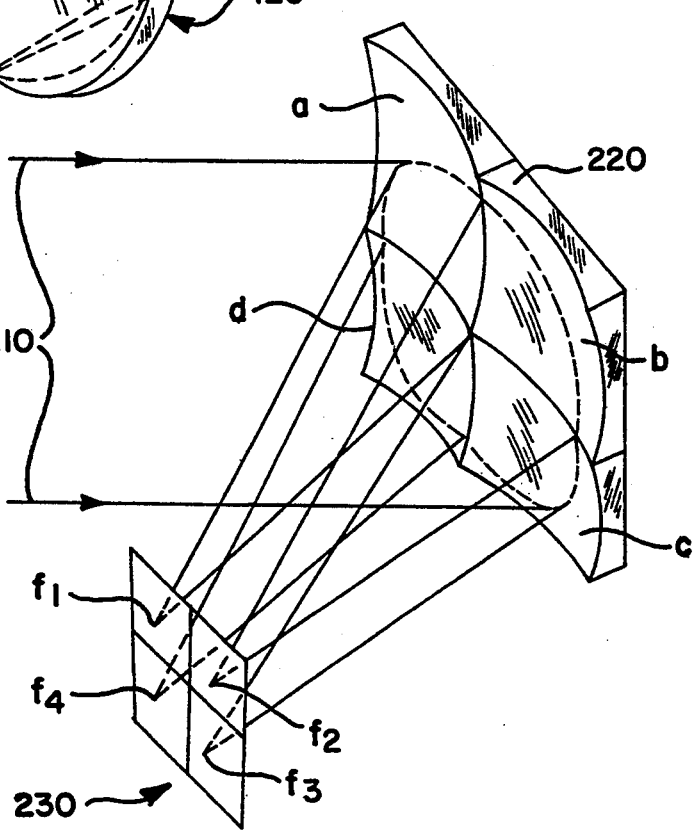
FIG. 3 is a perspective view of a collimated beam of light energy reflected from the segments of a multi-segmented mirror toward four focal points in the same plane.

In another embodiment of an optical system that divides a single light beam into a plurality of light beams, FIG. 3 depicts a light beam 210 that impinges upon reflective sections a, b, c and d, of a concave multi-segmented mirror 220. Each segment has a concave curvature. As a result, the partitioned light beams converge along an open or free beam path to focal points f1, f2, f3, and f4, corresponding to reflection from each of the reflective sections a, b, c and d. Each of the reflective sections a, b, c and d, is constructed from off-axis parabolic sections, so that the light ray reflected from a single off-axis parabolic section will converge to a single focus.

Other converging reflective sections, such as spherically symmetrical or parabolically symmetrical sections, can also be used. The focal point positions are determined by the choice of concavity. If identical sections are used, proper alignment of the sections can determine the position of the individual focal points. A plurality of converging sections will reflect light energy toward a corresponding equal number of distinct foci. The focal points (f1, f2, f3, and f4) of the multi-segmented mirror 220 are preferably constructed to lie in the same focal plane 230.

In an alternative embodiment, reflective sections a, b, c and d, can be planar with each section reflecting the light energy of a converging beam to one of the focal points (f1, f2, f3 and f4). The converging beam is achieved by placing a converging lens in the input beam path. The beam will continue to converge upon traversal of the planar mirrored sections.

FIG. 4 is a ray trace diagram of an optical system 300 that illustrates the utilization of a multi-segmented lens 320 to divide input light beam 310. The light beam 310 originates from a laser or optical fiber source (not shown). The path of the light beam 310 is represented by light rays a, b and c, where light ray a is coincident to the optical axis OA. In this embodiment, three optical elements, each of which has a proximal surface and a distal surface, act upon light beam 310. The light beam 310 enters the proximal surface of the diverging lens 311, composed of parallel light rays a, b, and c. The diverging light beam 312, consisting of rays b and c are diverted from the optical axis OA, as they exit the distal surface of the diverging lens 311 (with light ray a following optical axis OA). The expanded light beam 312 then impinges upon the proximal surface of converging lens 313, and converging light beam 314 exits through the distal surface of same, as indicated by light rays a, b, and c, in a generally parallel path toward multi-segmented lens 320.

Multi-segmented lens 320 is constructed from a plurality of segments, each having a convex proximal surface. A discontinuity exists at the interface between the segments. The distal surface of multi-segmented lens 320 is planar. Multi-segmented lens 320 divides the light beam 310 into two separate beams of light energy, a1 and b, and a2 and c, each of which converges along an open or free beam path to focal points f1 and f2, respectively, in space at focal plane 330.

FIG. 5 is a ray trace diagram depicting an optical system 400 that utilizes a multi-faceted lens 420 to divide the input light beam 410 into beams that converge at a first and second focal point, f1 and f2, respectively, at focal plane 430. Starting at the left of the ray trace diagram, the input light beam 410, composed of light rays a, b, c, impinges on the proximal surface of diverging lens 411 and exits the distal surface of the same, in a diverging path as represented by light rays b and c (with light ray a along optical axis OA). The diverging lens 411 is a plano-concave lens, with a planar or flat proximal surface and an inward or convex curvature at its distal surface. Several configurations for the diverging lens 411 exist, the plano-concave being shown by way of example only.

As examples of the light ray paths through diverging lens 411, light ray a traverses a path through the center of diverging lens 411, along the path of optical axis OA while second light ray b traverses a path at the upper boundary of the diverging lens 411, and third light ray c traverses a path at the lower boundary of the diverging lens 411. In a uniform medium, the direction of a light ray path can be defined by two orthogonal (perpendicular) distance coordinates relative to the optical axis OA. Snell's Law determines the light ray path as the light enters, proceeds and exits an optical component. The light ray path, as the light ray undergoes medium changes, is determined by consideration of the normal to the tangent of the optical surface which the light ray enters and that from which it is emitted. Of course, the choice of optical substrate medium, where each optical substrate medium has a specific index of refraction, is determined according to the constraints of Snell's Law.

Referring again to FIG. 5, second light ray b and third light ray c each bound a path which diverges outwardly from the optical axis OA of the distal surface of diverging lens 411, as represented by diverging beam 412. The path of the first light ray a is on optical axis OA, which is a common reference to the elements of the optical system 420. As the diverging beam 412 reaches converging lens 413, the light rays pass through the proximal surface of the converging lens 413, through the substrate medium, and exit from the distal surface of the converging lens 413. The light rays b and c are bent into a slightly converging path in relation to the optical axis OA as they exit from the distal surface of converging lens 413, represented by converging beam 414, and advance toward multi-faceted lens 420, while light ray a follows optical axis OA.

Multi-faceted lens 420 is a prism type optic with a flat or planar proximal surface and at least two distal facets, in this embodiment there is an upper facet and a lower facet. The light rays a1 and c are diverted from the lower facet to converge at focal point f1, and light rays a2 and b converge at focal point f2, all in focal plane 430.

However, in the present invention, the aforementioned multi-segmented or multi-faceted optics may have any number of segments or facets, in a pyramidal or symmetrical arrangement. The number of segments or facets determines the number of focal points in space where the partitioned paths of each converge. Table I, below, illustrates the relationship between the facet geometry and the focal spot array. It can be seen that the number of facets corresponds to the number of spots of the focal spot array.

TABLE I

Relationship Between Facet Geometry of a Multi-Faceted Optic and Focal Spot Arrays Resulting From Light Propagation Therethrough

| Facet Geometry | Number of Facets or Segments | Number of Focal Spots |
| --- | --- | --- |
| Biprism | 2 | 2 Spots |
| Triangular Pyramid | 3 | 3 Spots |
| Pyramid | 4 | 4 Spots |
| Pentagon | 5 | 5 Spots |
| Flat-Topped Pyramid | 5 | 5 Spots |
| Hexagonal Polycone | 6 | 6 Spots |

Faceted optics are commercially available from companies such as Laser Power Optics of San Diego, Calif. In specialized manufacturing processes, optics such as these are often fabricated by utilization of equipment such as a diamond fly wheel cutter, as is known in the art. Typical faceted optics are described in Danielewicz et al., "Innovative Optics for Shaping and Focusing Industrial CO2 Lasers" in *Proceedings of The International Society for Optical Engineering (SPIE), Volume 1024* (1988).

The proximal surface of an optical fiber is positioned at each focal point, as will be discussed in more detail later.

Each focal point has an associated spot size which generally depends on the dimensions of the optical system, the wavelength of the laser and the geometry of the multi-faceted or multi-segmented optic (i.e. the curvature of the distal surface and the dimensions thereof). There is an energy distribution associated with each focal point that can be described using the Gaussian beam approximation as described in Daly, "*Fiber Optics*", 6th printing, published by CRC Press, Inc. (1990).

The present invention is not intended to be limited to a single type of optic or optical system to divide a single input beam of light energy into a plurality of separate, output beams. Nor is the present invention intended to be limited to optics with any specific number of facets or segments. Also, it is not necessary for the amount of light energy in each output beam to be equal. The light energy in each path, which is generally dependent on the geometry of the dividing optic, can be altered by providing segments or facets of unequal surface areas that deflect various percentages of the light energy accordingly. A proportioning strategy to divide the light energy into paths with various energies can permit certain optical fibers to receive one quantity of light energy, while others receive a different quantity of light energy, at any desired percentage of the total energy.

In addition, the predominant spectral lines (i.e. the narrow range of wavelengths) which travel along each convergent path does not need to be the same from path to path. In other embodiments of the present invention, it may be useful to filter specific spectral lines in one or more of the light ray paths, thereby selecting a predetermined wavelength component for placement at a specified focal point. For example, one or more of the segments or facets of the multi-faceted lens 420 could be treated with an optical coating, as known in the art of optical component fabrication (and discussed earlier), to selectively filter out or permit the transit of certain specified wavelengths of light energy.

Also, one or more diverging, converging and/or collimating lenses can be used to expand, contract or parallelize the cross sectional area of the beam of light energy onto the proximal surface of one or more elements of the optical system, namely the dividing lens or any of the converging, diverging or collimating lenses.

Figure 6A:
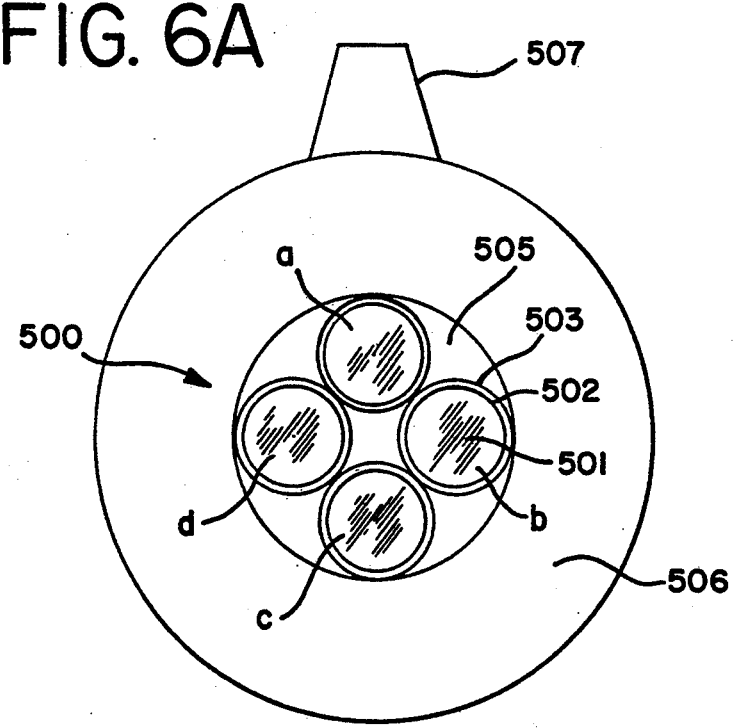
FIG. 6(A) is a front view of the end faces of a bundle of optical fibers.

FIG. 6(A) is a front view of the proximal end of a bundle 500 of optical fibers, with the optical fiber proximal end faces a, b, c and d, exposed. Each optical fiber of the bundle 500 consists of a core 501 and is surrounded by a thin layer of cladding 502. The cladding 502 has a slightly lower index of refraction as compared to the index of refraction of the optical fiber core 501 (as discussed later and illustrated in FIG. 11). A buffer coating 503 of teflon or other material may surround cladding 502. The bundle 500 of optical fibers are held together by a potting material 505. The bundle 500 of optical fibers, including the potting material 505, may be retained within a male cylindrical body 506. A locator key 507 is shown at 12 o'clock. Key 507 may be used to orient male cylindrical body 506 within a slot in a cylindrical female shaft (not shown).

Figure 6B:
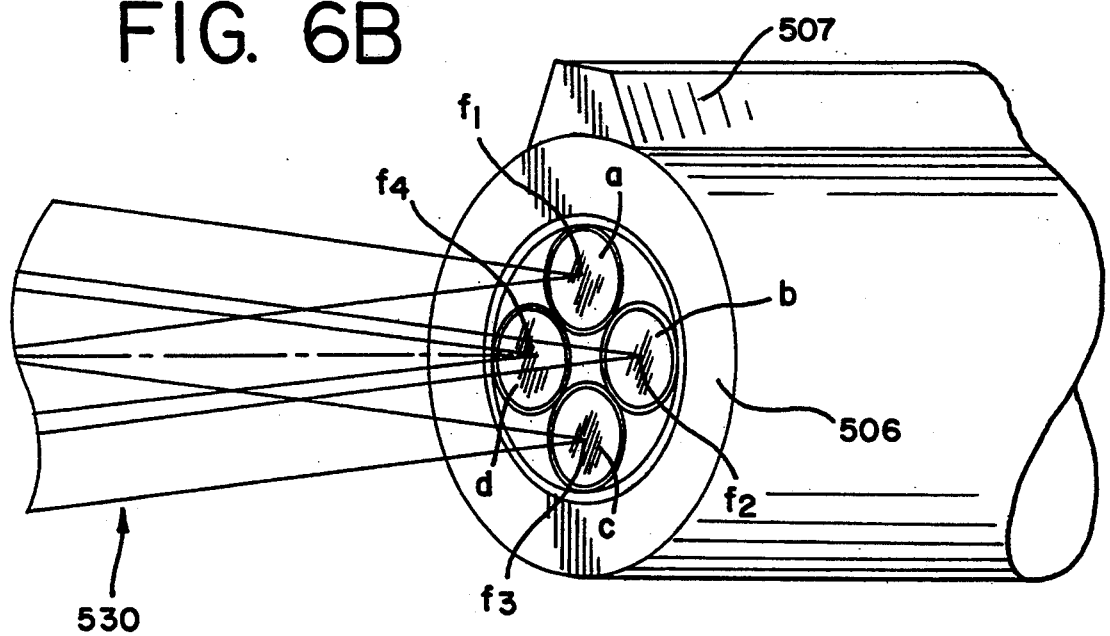
FIG. 6(B) is a perspective view of a divided beam of light energy, each portion of which is directed toward the end face of one of the optical fibers.

FIG. 6(B) is a perspective view of a plurality of light beams 530, with focal points f1, f2, f3 and f4, directed to corresponding optical fiber proximal end faces a, b, c, and d, respectively. As described above in FIG. 6A, the optical fibers may be held within the cylindrical male body 506. Locator key 507 may extend along a portion of the length of the cylindrical male body 506.

Figure 7A:
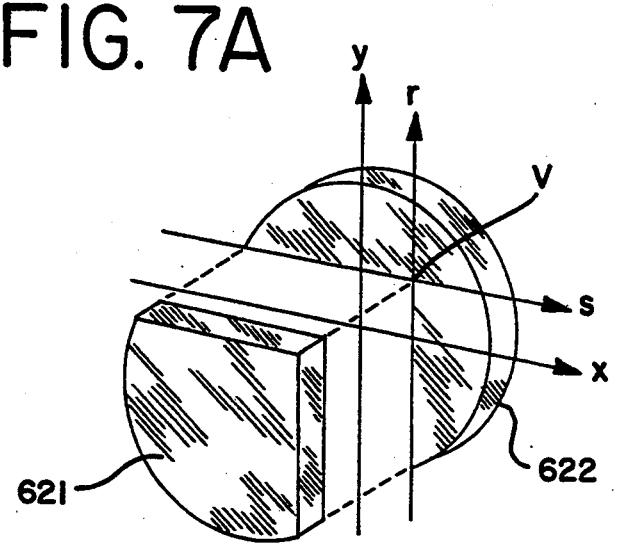
FIG. 7(A) is a front view of the off-axis partitioning of a cylindrically symmetrical converging lens for producing one segment of a four-segment lens.

The construction of a multi-segmented lens 620 is shown in FIG. 7(A). A segment 621 is cut from a circular plano-convex lens 622. However, several different types and shapes of optics can be utilized in this invention. Segment 621 is shown referenced against an x-y coordinate system, which is centered at the cylindrically symmetrical axis of the circular lens 622. Vertex v of segment 621 is located at an off axis location at the intersection of the lines r and s, in the first quadrant of the x-y coordinate system. The segment 621 is created from a precise cut of circular lens 622 along the planes bounded by lines r and s. In this embodiment of the present invention, segment 621 is a pie-shaped wedge with an angle of ninety degrees at the vertex V. A discontinuous, four-segment, clover shaped, multi-segmented lens 620 (as previously discussed) is formed from the placement of four such segments 621 in adjacent alignment. In other embodiments, there can be three segments with equal angular vertices, for example, each of one hundred and twenty degrees, five segments, each with angular vertices of seventy two degrees, etc. The angular vertices are determined by dividing three hundred sixty degrees by the number of segments. There can also be segments with unequal angular vertices for an unequal division of light energies, where it is desirable to have an unequal amount of light energy at one or more of the focal points.

Figure 7B:
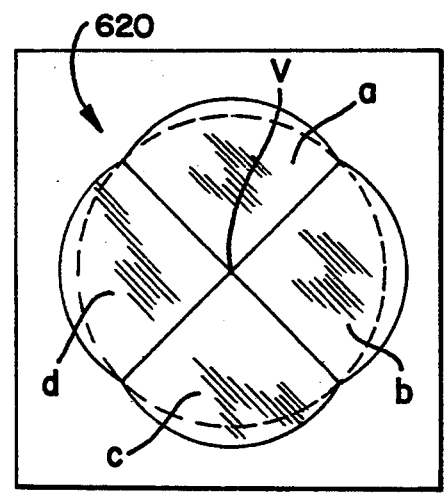
FIG. 7(B) is a front view of a set of four, off-axis shaped, converging lens sections which are fitted together to form a four segment lens.

FIG. 7(B) is a front view of a multi-segmented lens 620, which has been formed from four segments 621, a, b, c and d of the kind described in FIG. 7(A). The four segments a, b, c and d of multi-segmented lens 620 are fitted together in a pie-shaped arrangement with the vertex V of each sharing a common point. A light beam (not shown) entering the proximal surface of the multi-segmented lens 620 would be divided into four separate paths, with each path converging at a different point in space, preferably in the same focal plane.

Figure 8:
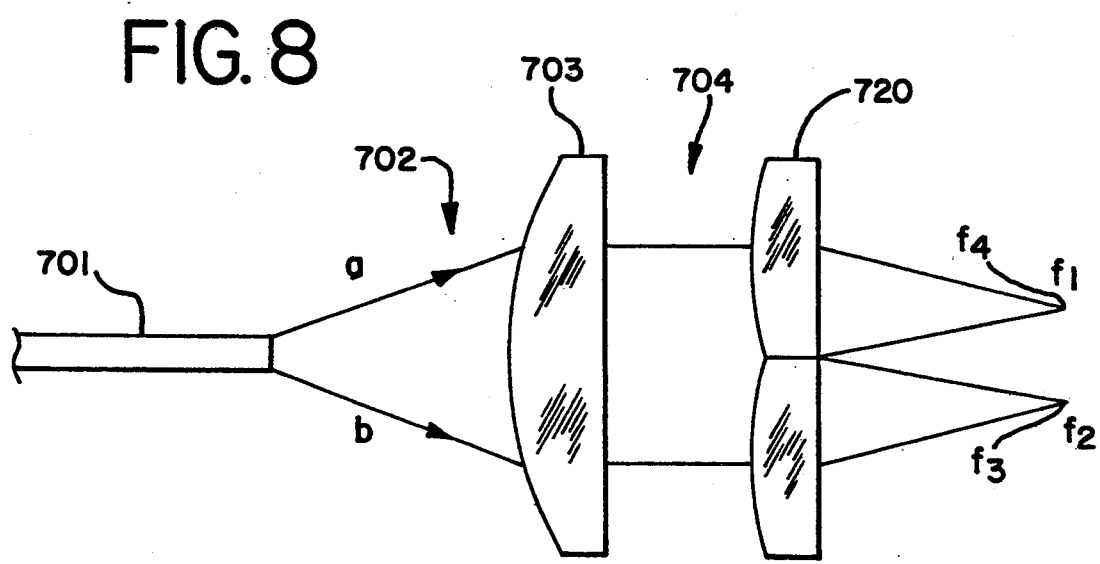
FIG. 8 is a side view of a diverging light beam emitted from an optical fiber that is collimated by a converging lens and divided by a multi-segmented lens.

A typical application of a multi-segmented lens 720 is shown in FIG. 8. A fiber optic 701 emits a divergent light beam 702, represented by light rays a and b. The divergent light beam 702 impinges on the proximal surface of the collimating lens 703 and exits the distal surface thereof as light beam 704, represented by parallel light rays a1 and b1, toward the multi-segmented lens 720. The multi-segmented lens 720 divides light beam 704 into four lesser beams which are converged to focal points f1, f2, f3 and f4, preferably in focal plane 730.

Figure 9A:
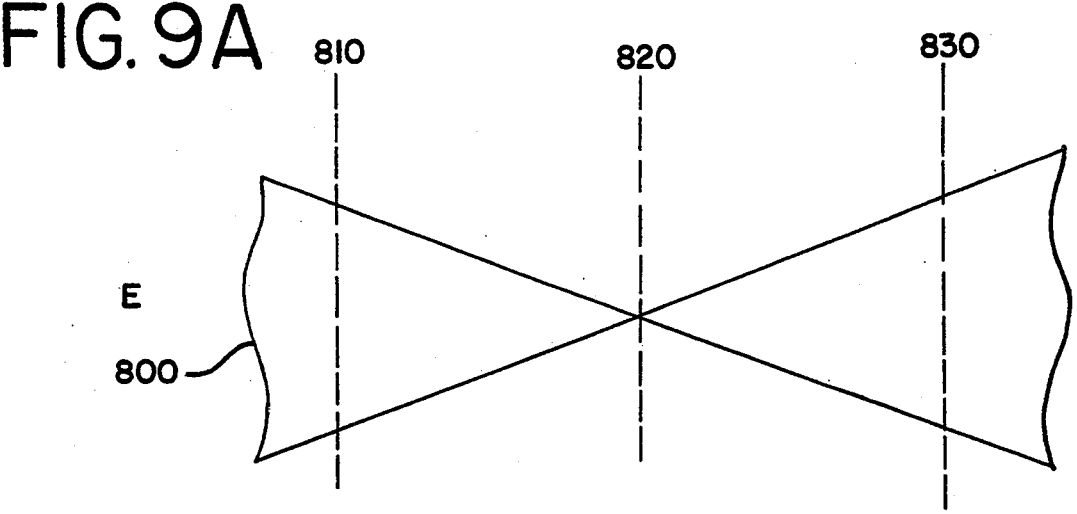
FIG. 9(A) is a diagram of an input beam of light energy converging to a focal point, showing the energy density at the focal point and at points before and after the focal point.

FIG. 9(A) is a diagram of a beam of light energy beam 800 converging at a focal point 820, at which the energy density is the highest. At planes 810 and 830, the energy density is relatively lower. In the case of a xenon chloride (excimer) laser at a wavelength of 308 nanometers, the energy density at the focal point 820 is, for example, approximately 10 joules per square millimeter, when the laser output is 300 millijoules per pulse, and at planes 810 and 830, the energy density is approximately 1 joule per square millimeter.

Figure 9B:
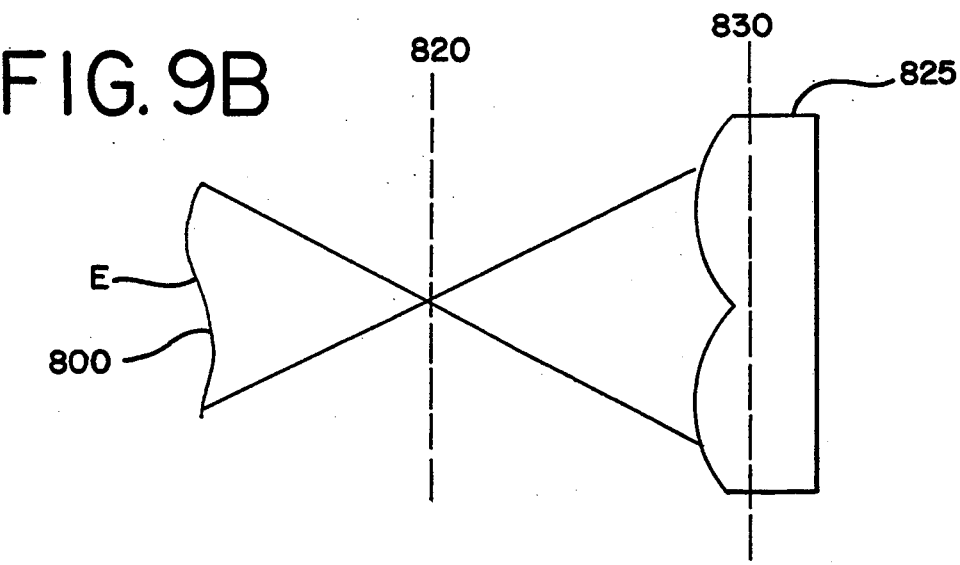
FIG. 9(B) is a diagram of a beam diverging from a focal point to a location at which the energy density damage threshold of the incident surface of an optical component in the path of the beam is not exceeded.

FIG. 9(B) illustrates the energy density relationship to optical component placement. A multi-segmented lens 820 (or a multi-faceted lens or other optical component) is positioned at plane 830, in the path of the light energy beam 800. The multi-segmented lens 820 is positioned away from the focal point 820, as the energy density at point 820 could damage its proximal surface, to a position at plane 830, where all of the incident light energy is captured, and where the energy density is below the damage threshold of its proximal surface.

Figure 9C:
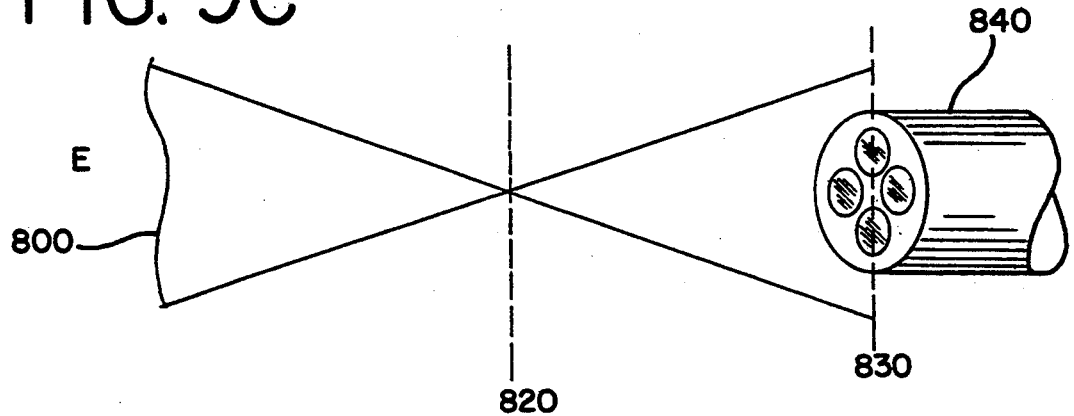
FIG. 9(C) is a diagram of a bundle of optical fibers placed in the beam path at a location where the damage threshold of the optical fiber incident surface is not exceeded.

In FIG. 9(C), a plurality of optical fibers in bundle 840 are positioned away from focal point 820, at a focal point 830 where the incident surfaces of the optical fibers in bundle 840 are not subject to damage.

Efficient positioning of optical components and optical fibers is constrained by the energy density of the light beam and the damage threshold of optical elements. The present invention is configured to accommodate a light beam of relatively high energy density, where the beam is divided into lesser beams of relatively lower energy density so as not to exceed the damage threshold of each optical element, while providing an increased transfer efficiency of optical coupling.

Figure 10:
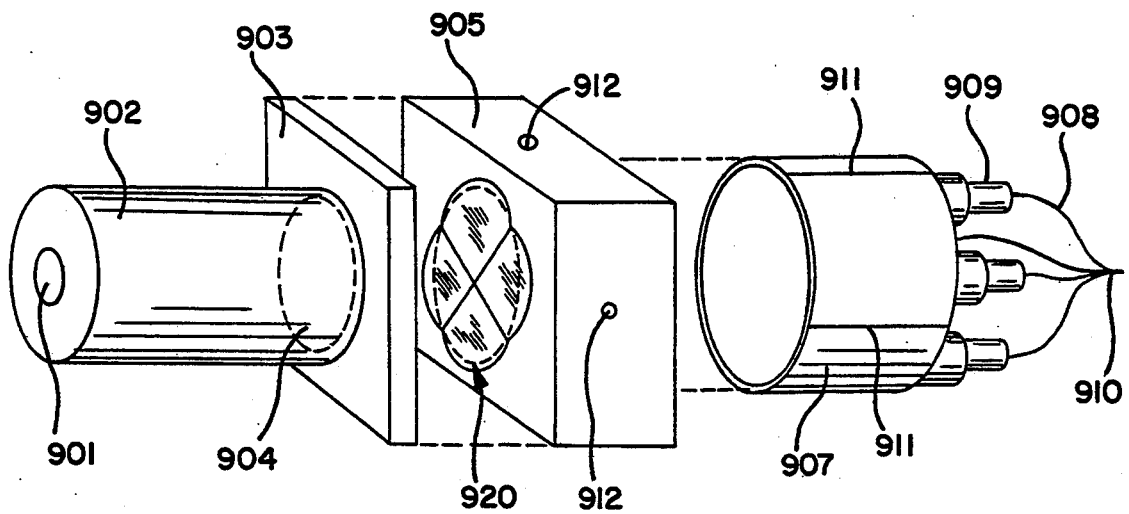
FIG. 10 is an exploded, perspective view of a preferred embodiment of the invention and depicts a housing for a beam expander, a housing for a multi-segmented or multi-faceted lens and a housing for a plurality of optical fibers.

In FIG. 10, a housing assembly containing the optical components of a preferred embodiment are shown. The individual housings are designed to retain the optics in fixed position while permitting alignment and fine adjustment of the optical components of the optical system.

Input port 901 is an opening in a housing 902 that is detachably mounted to a mounting plate 903. Housing 902 or mounting plate 903 can contain a converging, collimating and/or diverging lens or lenses 904. The input port 901 of the housing 902 can accept light energy from, for example, a laser or an optical fiber, each by an appropriate connector means as known in the art.

A multi-faceted or multi-segmented lens 920 (a multi-segmented mirror is likewise suitable, although this variation would involve a pivoted or fixed corner section, among other configurations, to provide traversal of the reflection angle at the surface of the mirrored sections) is mounted within optic housing 905 so that the light beam from the converging, collimating and/or diverging lens or lenses 904 impinges upon the proximal surface of the multi-segmented lens 920, discussed in detail above, and is partitioned into separate converging open or free beam paths.

Optic housing 905 attaches to the focusing housing 907, so that each of the light beams converge at the proximal end face of one of the individual optical fibers 908, each of which is held by an optical fiber connector 909, constructed in a manner that is known in the art.

In this, and similar embodiments of housings that retain the optical system, fibers and associated hardware, there is an open or free beam path between the multi-segmented lens and the proximal end faces of the optical fibers. The open or free beam path usually has an index of refraction having a value substantially that of air. However, in alternative embodiments, the open beam path of the region partially defined by the housing and disposed between the multi-segmented lens and the optical fibers can contain a fluid or gas with an index of refraction no more than approximately 1.34 (specifically intended to include water, which has an index of refraction of 1.33). Having a substance in the gas or liquid phase in this volume region provides predictable optical characteristics that are dependent on: (1) the index of refraction of the medium in the open or free beam path region, and (2) the shape, index of refraction, and the relative positioning between the multi-segmented lens and the proximal ends of the optical fibers. The substance in the open beam path can be chosen to provide an advantage of index matching, as explained by the well known relation for Fresnel surface reflection, to further reduce coupling losses.

The individual output optical fibers 908 can be grouped together into an output optical fiber bundle 910. The proximal end faces of the optical fibers 908 are positioned about the optical axis defined by the focal points of light emitted by multi-segmented lens 920. By sliding the focusing housing 907 forward and back, along grooves 911, which mate with keys (not shown) of optic housing 905, the proximal end faces of the optical fibers 908 can be precisely positioned at the plane of the focal points of light energy emitted from multi-segmented lens 920. When correctly positioned, focusing housing 907 can be fixed in place by set screws 912.

Housing 902, plate 903, optic housing 905 and focusing housing 907 may be built from separate precision machined metallic parts, composed of materials by example only, such as stainless steel or aluminum, and assembled with or without detachable coupling means to assure the correct alignment of the components.

Figure 11:
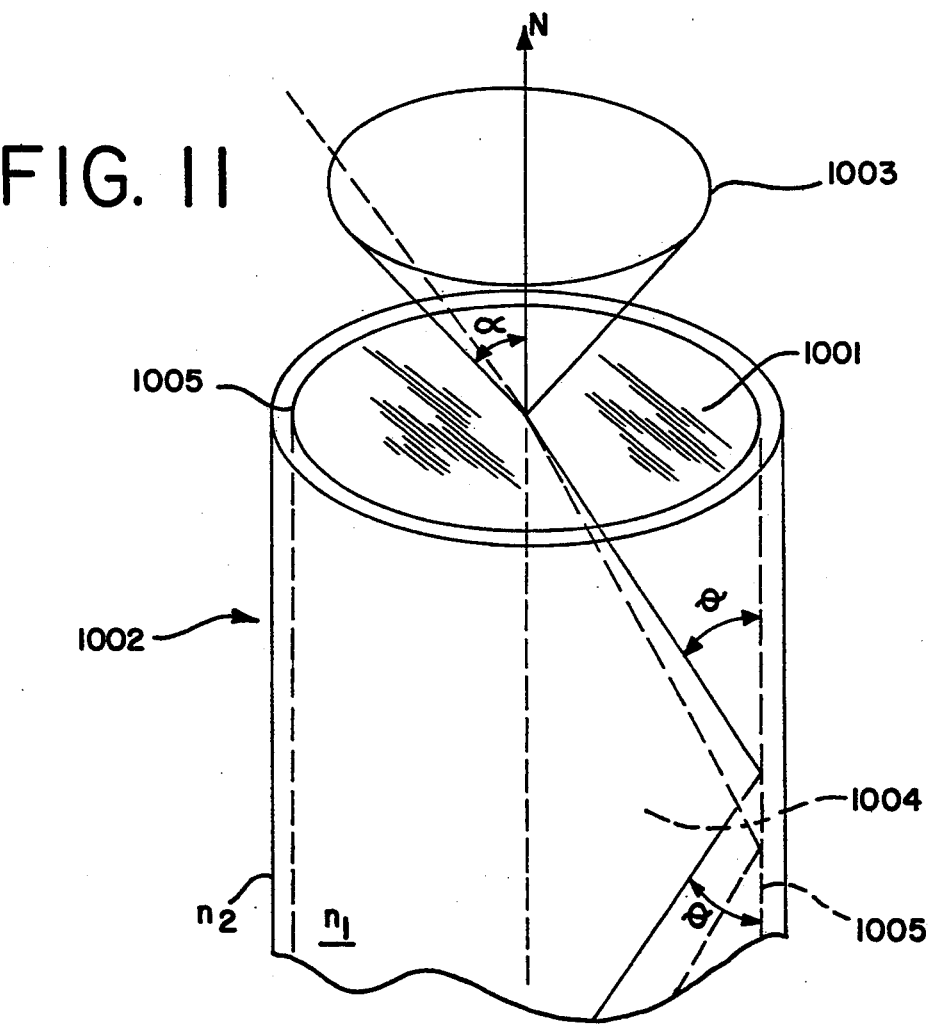
FIG. 11 is a diagram of a typical cone of acceptance at the end face of a fiber optic and the critical angle for total internal reflection of an incident beam of light energy.

FIG. 11 is a perspective diagram of the proximal end face 1001 of an optical fiber 1002. The cone of acceptance 1003 indicates the region where a beam of light energy could enter the core 1004 under the condition of total internal reflection. The cone of acceptance 1003 is well known in the art and is described in greater detail in *Galileo Electro-Optics Corp. Technical memorandum 200, "Fiber Optics: Multi-Mode Transmission"*. The core 1004 of the fiber optic 1002 is composed of a material with an index of refraction of n1, and core 1004 is surrounded by a cladding 1005 of lower index of refraction n2 (i.e. n1>n2), so that total internal reflection will occur for critical angles of incidence at the interface surface. The interface surface is the transition region between the cladding 1005 with an index of n2 and the core 1004 with an index of n1. Total internal reflection occurs under the constraint that the angle between the reflecting light ray and the interface surface is less than the critical angle complement (theta). In a condition of total internal reflection, the light reflects through the core 1004 of the fiber optic 1002 one hundred percent (neglecting the minimal losses due to an evanescent field). The critical angle complement (theta) can be readily calculated as a result of Snell's Law for boundary interfaces where the transition is from dense to rare. Once the critical angle complement is known, the angle (alpha) from the normal N of the fiber optic end face 1001 to the cone of acceptance 1003 can be calculated, again, as a result of Snell's Law of Refraction. The vertex of the cone of acceptance 1003 for total internal reflection can be depicted at all points on the surface of the fiber optic end face 1001 for all light rays entering the core 1004 of the fiber optic 1002.

In other embodiments of the present invention, the mechanical adjustments needed to position the fiber optic end faces of the receiving optical fibers in alignment with the focal points of a partitioned beam of light energy can be implemented with a set of electro-mechanical servo motors that shift the position of the optical fiber end faces in correct orientation according to a computer control system. Fine adjustments in positioning can be automatically implemented by a feedback system that can detect differences in fluence maxima and minima of the partitioned light beam as measured by a suitable detector. This information can be converted to signals which are understood by a servo motor controller. Automated systems of this type are usually processed and monitored by a computer in a manner known in the art.

Figure 12:
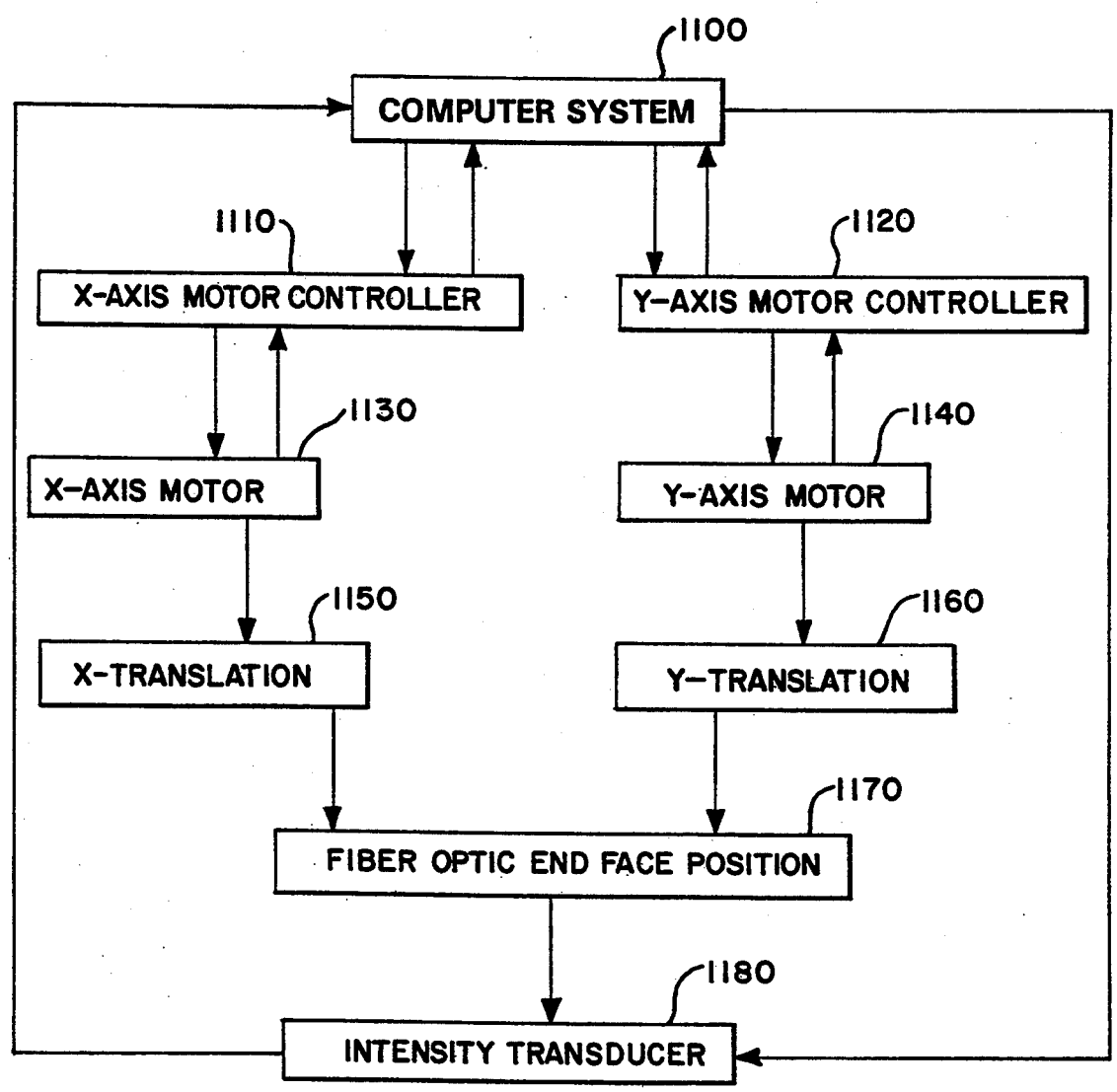
FIG. 12 is a block diagram of a feedback control system that adjusts the position of each of the optical fiber end faces.

FIG. 12 is a block diagram of a computer positioning system that can provide automatic adjustment of individual fiber optic end faces. A computer system 1100 is coupled, in two way communication, to an x-axis motor controller 1110 and a y-axis motor controller 1120. The x-axis motor controller 1110 and the y-axis motor controller 1120 are computer peripherals that control the x-axis motor 1130 and the y-axis motor 1140 respectively. Each motor is usually a stepper type servo motor that has a very accurate response to signals from computer system 1100. The intensity transducer 1180 is a computer peripheral that is optically coupled to each of the optical fibers in a manner known in the art, to detect increases or decreases in signal intensity transmitted through each optical fiber. The intensity transducer 1180 provides feedback stimuli. In an interchange, the computer system 1100 can send control signals to alert the peripherals, at the moment it is appropriate to effect a data transfer, either to send or to receive data. The peripherals respond to the computer control with a handshaking control signal to acknowledge the computer request. Alternatively, the peripherals can initiate the interchange. In the block diagram, the computer system 1100 is coupled to the x-axis motor controller 1110 and the y-axis motor controller 1120, and can send data signals that determine the direction of rotation and acceleration of each respective x-axis motor 1130 and y-axis motor 1140. The x-axis motor 1130 and the y-axis motor 1140 are mechanically coupled by a fine linkage of gears, in a manner known in the art, that provide an x-translation 1150 and a y-translation 1160, respectively, which adjusts the fiber optic end face position 1170.

The x-translation 1150 and the y-translation 1160 have a firm linkage with minimal backlash, so that fine adjustments are permitted when each motor is in clockwise or counter-clockwise rotation. An intensity transducer 1180 detects the intensity of each incident beam of light energy. The intensity transducer 1180, in response to a request by the computer system 1100, sends this information to the computer system 1100, where it is processed as a basis for determining the signals to the x-axis motor controller 1110 and y-axis motor controller 1120. The maximum signal transmission occurs when an optical fiber end face is at an optimal alignment.

A typical computer system flowchart for finding the maximum signal transmission (with respect to an x-axis servo motor control for the x-axis position and a y-axis servo motor control for the y-axis position), to assure the correct alignment of the fiber optic end face with the partitioned beam of light energy, is shown in FIG. 13. With an x-axis and a y-axis hardware linkage coupled to an x-axis and y-axis motor, the computer program algorithm provides for the detection of signal maxima by permitting the motor to continue to rotate, while the intensity of the signal either remains constant, or increases. If the intensity of the signal decreases by a level greater than the resolution interval, the motor reverses in direction. The method involves several iterations of successively finer resolution intervals which are set by the loop counter.

The program sequence is as follows. At the start of the computer program, there is an initialization block 1210 which provides for setting the loop counter to value 1, and also provides for defining the initial resolution interval which is related to the sensitivity of the intensity meter. The loop counter value increases as a number of iterations proceed, as the intensity converges to a peak value by decreasing the resolution interval at each iteration. The resolution interval is a coarseness factor utilized for comparison of relative intensity values to previously stored values. After initialization in block 1210, the initial intensity is read and set to value I0 at blocks 1220 and 1230. A "rotate motor clockwise" command is generated in block 1240 to accelerate the motor in the clockwise direction, which moves the linkage retaining each optical fiber end face. A new intensity resulting from the clockwise rotation of the motor is read at block 1250. This intensity value is stored in variable I1 at block 1260. At conditional block 1270 I1 is compared to I0. On the condition that I1 is greater than or equal to I0 is a true statement, (where the intensity is increasing or remaining the same relative to the previously stored value in I0), the motor will continue to rotate, subsequent to setting I0 (the previous value) equal I1 (the new intensity value) 1280 so that the same comparison can be made again later. On the condition that the statement at block 1290 is false, where the intensity significantly drops (as defined by the resolution interval factor), it is recognized that the intensity has exceeded the peak and the direction of the motor is then reversed at block 1290. A new relative intensity is read at block 1300 and assigned to variable I2 at block 1310. At conditional block 1320, variable I2 is compared to previously stored intensity value I1, to determine whether or not the intensity is remaining the same or increasing. If condition at block 1320 is true, the motor continues to rotate counterclockwise subsequent to setting the present value of intensity I2 to the previously stored value I1 at block 1330 for future comparison. If conditional block 1320 is false, the intensity level has dropped and the loop counter is incremented at block 1340 and then the loop counter value is compared to a fixed number (e.g. five iterations), at block 1350, whereupon the program will end so that program will not loop infinitely. If the number of iterations have not been exceeded, the resolution interval is decreased at block 1370 and the program branches back for a repeat of the clockwise and counter clockwise motor rotation procedure, starting at block 1220.

The control system responsiveness is set by the loop counter and resolution interval variables which can provide several iterations of successively finer resolution values for comparison to assure that signal maxima have been converged to. In the example shown, the computer flowchart ends after the system has looped five times, permitting the resolution interval to be decreased five times, as arbitrarily set by a loop counter value of five. The aforementioned description of a electro-mechanical servo motor control system responsive to a feedback loop is illustrated for example only, and in principle can be adapted to adjust any of the various securement means of the fiber optic end faces to facilitate the light energy coupling, by maximizing the intensity signal transfer, of the present invention.

In certain surgical applications of the present invention, a second laser source, such as a low power, red helium-neon laser producing light energy at a wavelength of 0.633 microns, can be combined with the surgical laser beam, in a manner known in the art, to assist the surgical instrument user to guide the surgical laser beam, which may be invisible, to the target tissue. If the two wavelengths are combined in the same coincident beam, as known in the art, it is possible to transmit the light energy of the visible wavelength along the same path as the light energy of the invisible wavelength. In fact, some medical applications of lasers may simultaneously require the delivery to tissue of more than one wavelength of light energy, such as in U.S. Pat. No. 4,791,927 to Menger, entitled "Dual-Wavelength Laser Scalpel", to both cut and cauterize efficiently. For this reason, the optical system 20 of the present invention is not limited to the transmission of a single wavelength of light.

Lasers, optical fibers, lenses, housings, and other components of the optical system are known in the art, and are not described in detail and can be used in alternative combinations in practicing the invention.

The foregoing description of the preferred embodiments of the invention have been presented for purposes of illustration and description. They are not intended to be exhausted or to limit the invention to the precise forms disclosed, and obviously many modifications and variations are possible in light of the above teaching. The embodiments were chosen and described in order to best explain the principles of the invention and its practical application to thereby enable others skilled in the art to best utilize the invention in various embodiments with various modifications as are suited to the particular use contemplated. It is intended that the scope of the invention be defined by the claims appended thereto.

What is claimed is:

1. A device for optically coupling light energy which comprises:

a. a housing defining an input port for a beam of light energy and a plurality of lesser beam output ports, wherein each of said lesser beam output ports includes a female connector means to which a male optical fiber connector means is detachably coupled;

b. an optical means, retained within the housing, for dividing the beam of light energy into a plurality of lesser beams, each of the lesser beams being directed to a separate focal point;

c. a plurality of optical fibers having respective proximal end faces, and at least one proximal end face of one of said optical fibers being positioned at about the focal point of one of said lesser beams defining an incident beam cone of acceptance for said one of the lesser beams;

d. an open beam path defined by the housing between the optical means and the proximal end faces of the optical fibers; and e. means for adjusting the position of each male connector means so that the end face of the optical fiber therein can be positioned at the focal point of one of the incident lesser beams.

2. The device, in accordance with claim 1, wherein the adjusting means is comprised of a slot and key means, said adjusting means being detachably fixed in place with set screws.

3. The device, in accordance with claim 1, wherein the adjusting means is an electro-mechanical servo motor control system responsive to input from a computer based on feedback information as to the amount of energy delivered to the optical fiber in the male connector means.

4. The device, in accordance with claim 1, where at least one element of the optical means has a thin film coating on its proximal surface to enhance transmission at the wavelength of the light energy therethrough.

5. The device, in accordance with claim 1, wherein the core diameter of each of the optical fibers is at least as large as the diameter of the incident lesser beam at the focal point thereof, and where the energy density of said incident lesser beam at said focal point is below the damage threshold of the proximal surface of said optical fiber.

6. A coherent light source to optical fiber coupling system which comprises:
   a. a housing;
   b. a multi-segmented lens, retained within the housing, for dividing a beam of light energy from a coherent light source into a plurality of lesser beams of light energy about an optical axis, each lesser beam being focused toward a point in space;
   c. a number of optical fibers substantially equal to the number of segments of the multi-segmented lens, said optical fibers together providing an array of substantially coplanar fiber optic end faces about said optical axis at a predetermined distance from said multi-segmented lens, each of said end faces being positioned at about the focal point of one of said lesser beams of light energy, each of the proximal end faces of said optical fibers defining an incident beam cone of acceptance for one of the lesser beams; and,
   d. an open beam path, defined by the housing, along a medium having an index of refraction not greater than about 1.34; said beam path existing between the multi-segmented lens and the proximal end faces of the optical fibers.

7. The device, in accordance with claim 6, where the input beam of light energy is divergently emitted from the distal end of an optical fiber onto the proximal surface of a converging lens.

8. The device, in accordance with claim 6, where a converging lens contracts the cross sectional area of the input beam of light energy onto the proximal surface of the multi-segmented lens.

9. The device, in accordance with claim 8, where a diverging lens expands the cross sectional area of the beam of light energy onto the proximal surface of the converging lens.

10. The device, in accordance with claim 6, where the multi-segmented lens is comprised of a plurality of wedge shaped convergent lens sections.

11. A coherent light source-to-optical fiber coupling system which comprises:
    a. a housing;
    b. a multi-faceted lens, retained within the housing, for dividing a beam of light energy from a coherent light source into a plurality of lesser beams about an optical axis;
    c. a number of optical fibers substantially equal to the number of distal facets of the multi-faceted lens, said optical fibers together providing an array of substantially coplanar fiber optic end faces about said optical axis at a substantially fixed distance from said multi-faceted lens, each of said end faces being positioned at the focal point of one of said lesser beams of light energy, each of the proximal end faces of said optical fibers defining an incident beam cone of acceptance for one of the lesser beams; and
    d. an open beam path, defined by the housing, along a medium with an index of refraction not greater than about 1.34; said beam path existing between the multi-faceted lens and the proximal end faces of the optical fibers.

12. The device, in accordance with claim 11, where a converging lens contracts the cross sectional area of the beam of light energy onto the proximal surface of the multi-faceted lens.

13. The device, in accordance with claim 12, where a diverging lens expands the cross sectional area of the beam of light energy onto the proximal surface of the converging lens.

14. The device, in accordance with claim 12, where the input beam of light energy is divergently emitted from the distal end of an optical fiber.

15. The device, in accordance with claim 11, where the multi-faceted lens is comprised of a flat proximal surface and at least two distal facets.

16. A coherent light source to optical fiber coupling system which comprises:
    a. a housing;
    b. a multi-segmented mirror, retained within the housing, each segment of which has a proximal surface to divide the beam of light energy into a plurality of lesser beams;
    c. a number of optical fibers substantially equal to the number of segments of the multi-segmented mirror, each of said optical fibers having an end face positioned at about the focal point of one of said lesser beams of light energy, each of the end faces of said optical fibers defining an incident beam cone of acceptance for one of the lesser beams; and
    d. an open beam path, defined by the housing, along a medium with an index of refraction not greater than about 1.34; said beam path existing between the multi-segmented mirror and the proximal end faces of the optical fibers.

17. The device, in accordance with claim 16, where the multi-segmented mirror is constructed from a plurality of off-axis parabolic sections.

* * * * *